United States Patent [19]

Taylor

[11] Patent Number: 5,562,102
[45] Date of Patent: Oct. 8, 1996

[54] MULTIPLE BIOPSY DEVICE

[76] Inventor: Thomas V. Taylor, 2002 Holcombe Blvd., Houston, Tex. 77030-4298

[21] Appl. No.: 342,723

[22] Filed: Nov. 21, 1994

[51] Int. Cl.$^6$ .................................................. A61B 10/00
[52] U.S. Cl. ............................................................ 128/751
[58] Field of Search .................................. 128/751–754; 606/167, 170, 205, 206

[56] References Cited

U.S. PATENT DOCUMENTS

| | | | |
|---|---|---|---|
| 3,924,608 | 12/1975 | Mitsui | 128/751 |
| 4,427,014 | 1/1984 | Bel et al. | 128/751 |
| 4,817,630 | 4/1989 | Schintgen et al. | 128/751 |
| 5,052,402 | 10/1991 | Bencini et al. | 128/751 |
| 5,195,533 | 3/1993 | Chin et al. | 128/754 |
| 5,318,589 | 6/1994 | Lichtman | 128/751 |
| 5,385,570 | 1/1995 | Chin et al. | 128/751 |

OTHER PUBLICATIONS

Olympus Corporation, 1985, pp. 1–2, (sales brochure).
Medical Engineering Laboratory, May 1993, p. 1, (sales brochure).

*Primary Examiner*—Max Hindenburg

[57] ABSTRACT

A multiple biopsy forceps and method for obtaining a biopsy are disclosed. The forceps comprises an outer tube which can be passed through a biopsy channel of an endoscope and an inner tube concentric with the outer tube and slideably received therein. The tubes slide with respect to each other to operate a set of jaws which can be positioned to grasp and remove a tissue sample for biopsy. The grasped tissue sample is then transfixed by a needle at the end of a wire which is slideably mounted in the inner tube and positioned between the jaws. The needle is advanced and retracted with the opening and closing of the jaws. After one tissue sample is removed, the forceps is repositioned at a second tissue area from whence another tissue sample can be taken in similar fashion. The forceps is not withdrawn from the endoscope until a desired number of tissue samples for multiple biopsies have been taken, thus eliminating the need for the repeated withdrawal and feed of the forceps down the biopsy channel during a single endoscopic examination.

21 Claims, 3 Drawing Sheets

MULTIPLE BIOPSY DEVICE

FIELD OF THE INVENTION

This invention relates to a biopsy forceps and, more specifically, to a biopsy forceps capable of obtaining multiple tissue samples in a single passage through an endoscope.

BACKGROUND OF THE INVENTION

Gastroenterologists, surgeons, and other physicians commonly obtain tissue samples for biopsy when examining interior parts of the body using an endoscope. Modern endoscopes are usually flexible instruments comprising a fiberoptic viewing system and a tubular channel through which biopsy forceps can be passed to obtain the samples. Prior art biopsy forceps are designed to obtain a single small piece of tissue on each passage through the endoscope. Such single pass forceps, however, are time consuming to use since clinicians frequently require multiple biopsies of a diseased area in order to gather adequate pathological or other scientific information and then the instrument must be passed in and out of the endoscope for each biopsy specimen. In addition when single pass forceps are used, the endoscope must be realigned to the tissue location in question for each specimen.

Prior art biopsy forceps have typically been constructed from surgical stainless steel making such instruments expensive to produce, and requiring sterilization procedures after each use while not fully eliminating risk of the spread of infection. Stainless steel forceps are, in addition, frequently difficult to pass along the endoscope channel when the endoscope must be acutely angled to access a lesion.

Thus, there is a need in the art for a biopsy forceps instrument which enables a clinician to obtain multiple tissue samples per each pass through the endoscope to increase the speed and simplicity of the procedure and reduce patient discomfort.

SUMMARY OF THE INVENTION

A multiple biopsy forceps of the present invention allows an endoscopist to take several separate tissue specimens in an ordered, identifiable fashion per insertion through the endoscope channel. By eliminating additional forceps feed, withdrawal and tissue realignment steps of a multiple biopsy procedure, the time spent for the procedure and patient discomfort can be greatly reduced. In addition, by making the present forceps preferably disposable rather than from the stainless steel of non-disposable models, difficulty in feeding the instrument through the biopsy channel particularly when the endoscope is acutely angled can be greatly reduced.

As one embodiment, the present invention provides a multiple biopsy forceps for obtaining multiple tissue samples for biopsy through a biopsy channel of an endoscope. As a first element, a tubular body having a length and outside diameter for passage through the biopsy channel is provided. A set of jaws mounted on a distal end of the tubular body and a jaws operating means are provided to grasp and remove a tissue sample. A needle centrally received through the tubular body and slideable therethrough is provided to transfix the tissue sample grasped by the jaws. A retaining element adjacent a distal end of the needle is provided to sequentially collect tissue samples on the needle. A proximal activating handle is provided for operating the jaws and needle.

As a preferred arrangement, the present invention provides a multiple biopsy forceps for obtaining multiple tissue samples for biopsy through a biopsy channel of an endoscope including an outer tube having a length and outside diameter for passage through the biopsy channel. An inner tube is concentric with the outer tube and slideably received therein. A set of jaws mounted on a distal end of one of the tubes operable by longitudinally sliding the inner and outer tubes with respect to each other is provided to grasp and remove a tissue sample. A needle centrally received through the inner tube and slideable therethrough is provided to transfix the tissue sample grasped by the jaws. A retaining element adjacent a distal end of the needle is provided to sequentially collect tissue samples on the needle. A proximal activating handle is provided for operating the inner and outer tubes, jaws and needle. The forceps which are preferably disposable can include graduation markings on the tubes for identifying the tissue location of each tissue sample collected. The needle is attached at a distal end of a wire slideably mounted in the inner tube and the proximal handle manually advances and retracts the wire in sequence with the closing and opening of the jaws.

The inner and outer tubes are preferably made of a substantially rigid plastic material which is flexible along the biopsy channel of the endoscope. The jaws are preferably cusp shaped, include a cutting edge and are made from a metallic or ceramic material. Alternatively, the jaws can be talon shaped. The jaws are preferably attached to the inner tube and are closed by slideably retracting the inner tube with respect to the outer tube or slideably advancing the outer tube with respect to the inner tube. The retaining element can comprise barbs or a needle with a helical configuration.

In another embodiment, the present invention provides a method for obtaining multiple tissue biopsies of an organ through an endoscope in the following sequential steps: In step (a), an endoscope having a biopsy channel is inserted to visualize an area to be biopsied. In step (b), an outer tube is inserted through the biopsy channel, the outer tube including an inner tube concentric therewith and slidably received therein. In step (c), jaws mounted on a distal end of one of the tubes are placed in contact with tissue to be biopsied, the jaws operable by longitudinally sliding the inner and outer tubes with respect to each other. In step (d), the jaws are operated to grasp a sample of the tissue to be biopsied. In step (e), the grasped tissue is transfixed with a needle for engaging the tissue sample with a retaining element thereon, the needle centrally received through the inner tube and slideable therethrough. In step (f), sequential tissue samples are collected on the needle by repeating steps (c) through (e). In step (g), the biopsy forceps is withdrawn from the biopsy channel to retrieve the tissue samples. The method preferably includes the step of reading graduation markings on the tubes for identifying the tissue location of each tissue sample collected. The jaw operating and tissue transfixing steps (d–e) are preferably effected by manipulating a proximal activating handle.

In a preferred embodiment, the jaws are preferably attached to the inner tube and the operating step (d) preferably includes the step of slideably retracting the inner tube with respect to the outer tube or slideably advancing the outer tube with respect to the inner tube to close the jaws. The needle is preferably attached to a distal end of a wire slideably mounted in the inner tube and the transfixing step (d) preferably includes manually advancing and retracting the wire in sequence with the jaws operating step.

DETAILED DESCRIPTION OF THE INVENTION

Figure 1:
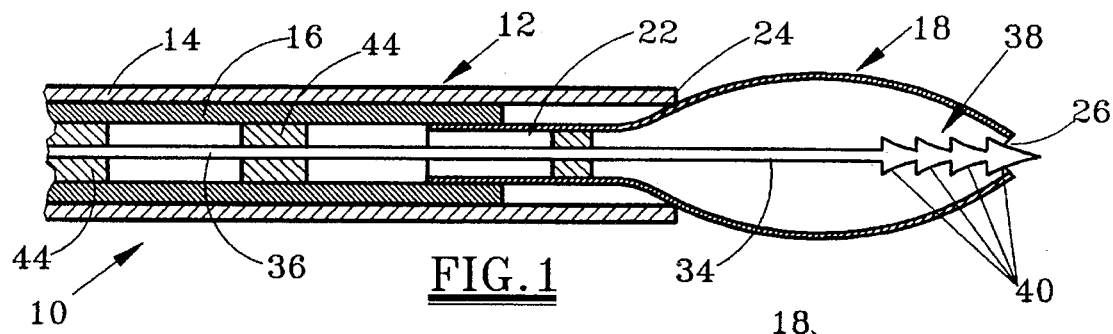
FIG. 1 is a side cross-sectional view of the distal end of the multiple biopsy forceps of the present invention showing a needle having a barbed retaining element and the relative positions of the outer and inner tubes, jaws and needle with the jaws closed to obtain a tissue sample for biopsy.
Figure 2:
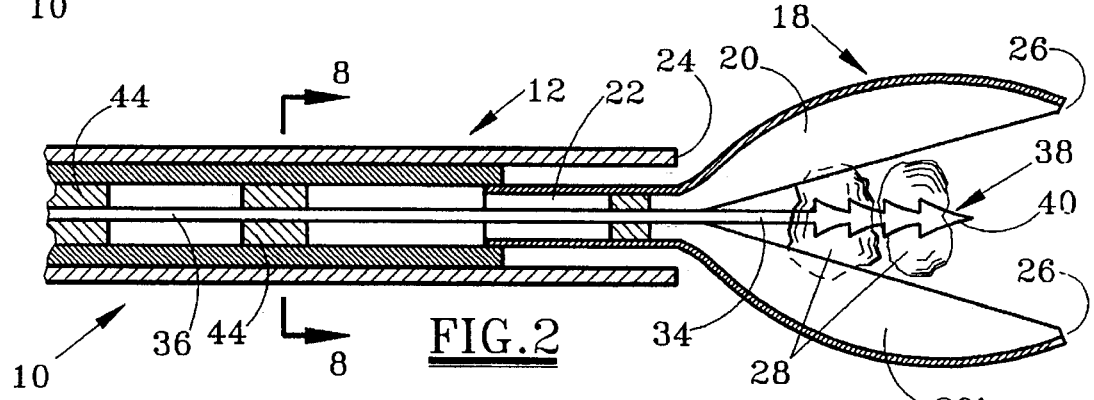
FIG. 2 is a side cross-sectional view of a distal end of the multiple biopsy forceps of FIG. 1 showing the relative position of outer and inner tubes, jaws and needle with the jaws opened and two sequential tissue samples retained for biopsy.
Figure 3:
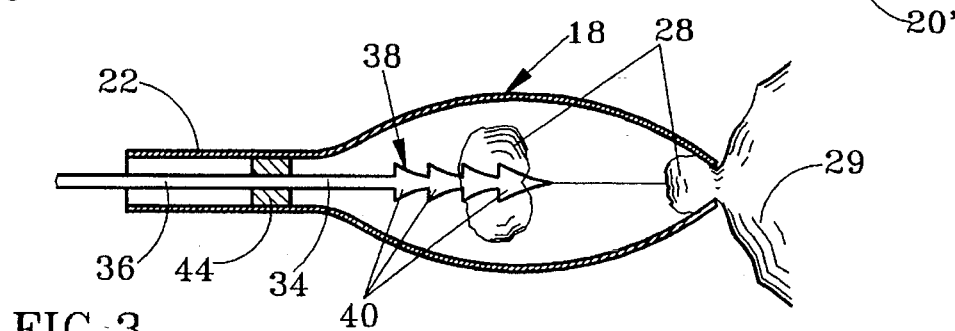
FIG. 3 is side cross-sectional view of the jaws of the multiple biopsy forceps of FIG. 1 shown grasping a tissue sample prior to removal.
Figure 4:
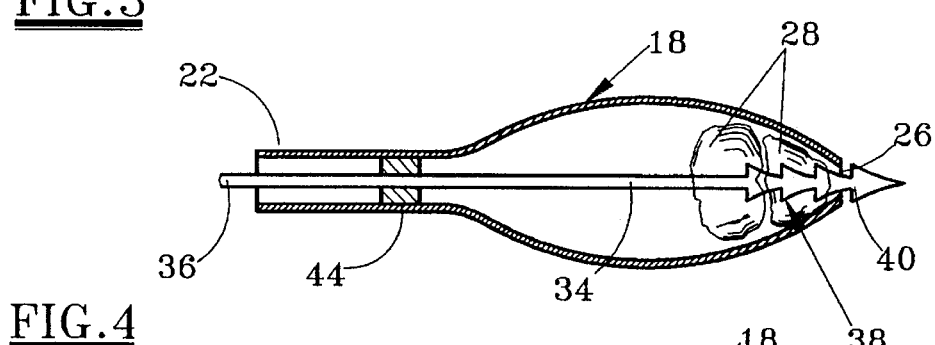
FIG. 4 is a side cross-sectional view of the jaws of FIG. 3 with the needle advanced through the jaw opening with the removed tissue sample transfixed.

The multiple biopsy forceps of the present invention suitable for use with an endoscope permits the clinician to obtain necessary tissue samples for biopsy and disease determination with a single pass through the endoscope. Use of the present forceps can reduce equipment usage and operating time for biopsy procedures and reduce patient discomfort.

Referring to FIGS. 1–8, wherein like numerals reference like elements, the forceps 10 of the present invention is a flexible, tubular medical instrument suitable for being passed down a biopsy channel (not shown) of an endoscope (not shown). The forceps 10 can be used to obtain multiple tissue samples per pass for biopsy of a potentially diseased tissue observed using the endoscope. The endoscope, as is well known in the art, generally comprises a tubular body having an annular biopsy channel for the biopsy forceps and a fiber optic cable for viewing the interior regions of the body. The endoscope is typically passed down the pharynx or up through the rectum to observe the interior regions of the gastrointestinal tract. If a biopsy is needed, the medical practitioner then inserts the biopsy forceps through the biopsy channel.

To effect slideable insertion through the biopsy channel, the forceps 10 comprises a flexible, tubular body 12 having a suitable length and outside diameter. The body 12 is preferably made up of an outer tube 14 and a concentric inner tube 16 slideably received therein. Relative position of the outer and inner tubes 14, 16 with respect to each other can be effected by a scissor-type handle 17 disposed at a proximal end of the forceps 10. The operation of such a proximal handle 17 is well known in the art. Generally, the handle 17 comprises two pivotably coupled, hand operated legs 19, 19' having a distal end 21 attached to the proximal end of the outer and inner tubes 14, 16. Manipulation of the handle 17 pivots the legs 19, 19' and imparts a change of position at respective distal ends 21. Pivoting of the ends 21, in turn, imparts a relative longitudinal position change of the outer and inner tubes 14, 16 with respect to each other.

A set of jaws 18 is mounted at a distal end of the tubular body 12. The jaws 18 comprise upper and lower cusps 20, 20' hinged at a neck 22 under spring tension so that the cusps 20, 20' have an open bias when no force is exerted thereon. While the jaws 18 can be attached to either the outer or inner tubes 14, 16, the jaws 18 are preferably mounted to the inner tube 16 for simplicity of operation by fixedly inserting the neck 22 into the annular region of the inner tube 16. Longitudinally sliding the inner and outer tubes 14, 16 relative to each other draws the neck 22 into the annular region of the outer tube 14 and causes an end wall 24 thereof to exert sufficient force on the spring biased cusps 20, 20' to effect closure of the jaws 18. The jaws 18 are typically made of a metallic material such as stainless steel to impart a spring bias to the cusps 20, 20' or a ceramic material.

Alternatively, the body 12 is made up of an outer tube 14 having a cable actuator (not shown) disposed therein. The operation of cable type actuators is well known. Generally, the cable actuator (not shown) includes a cable in a sheath attached at a distal end thereof to a hinge (not shown) of a spring biased jaws (not shown) so that relative change of position of the cable in the sheath effects closure of the jaws. Typically, the cable can also be spring biased and operated by a handle (not shown) at a proximal end thereof outside the endoscope.

The jaws 18 have a mouth 26 suitable for grasping a tissue sample 28 for biopsy from an organ wall 29 when the jaws 18 are closed. The mouth 26 includes a pair of pincer members 30 located on either side of an opening 32 through which a needle 34 can pass to retain the acquired tissue sample 28.

The needle 34 is disposed in the jaws 18 at a distal end of a wire 36 extending the length of the forceps 10. The needle 34 preferably includes a retaining element 38 suitable for retaining a plurality of tissue samples 28 acquired by repeated use of the forceps 10 per pass through the endoscope. The retaining element 38 can be formed of a series of barbs, hooks, helical turns of the needle, and the like. A succession of barbs 40 is preferred. The barbs 40 have a size suitable to pass through the opening 32 of the jaws 18 to transfix the grasped biopsy sample 28.

The wire 36 extends from the barbs 40 through the annulus of the inner tube 16 to a handle 42 at a proximal end of the forceps 10. The wire 36 is preferably held concentric in the inner tube annulus by a plurality of suitably spaced apart spacer elements 44 to avoid the possibility of kinks developing therein. The needle 34 is advanced and retracted a fixed distance in a reciprocating fashion as needed to transfix the biopsy sample 28 by manipulating the handle 42. In this manner, the needle 34 is operable independently of the jaws 18 to transfix the specimen secured by the jaws by the jaws 18.

Figure 9:
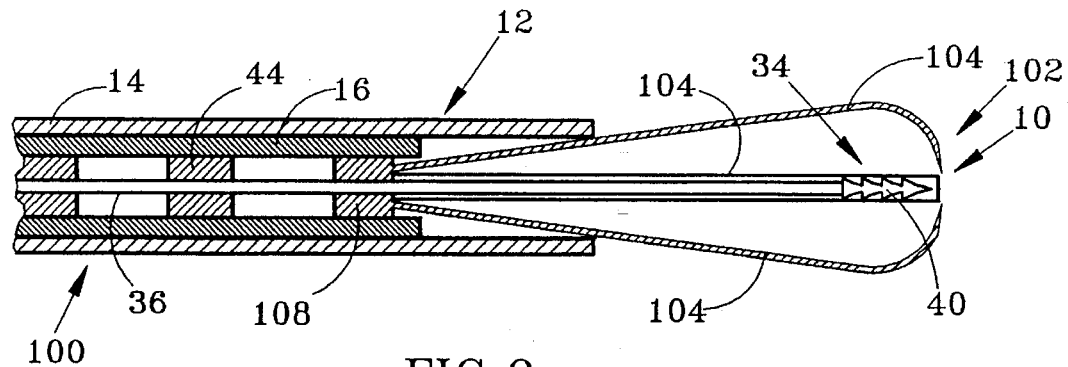
FIG. 9 is a side cross-sectional view of the distal end of another embodiment of the multiple biopsy forceps of the present invention showing a talon shaped jaws with the jaws closed.
Figure 10:
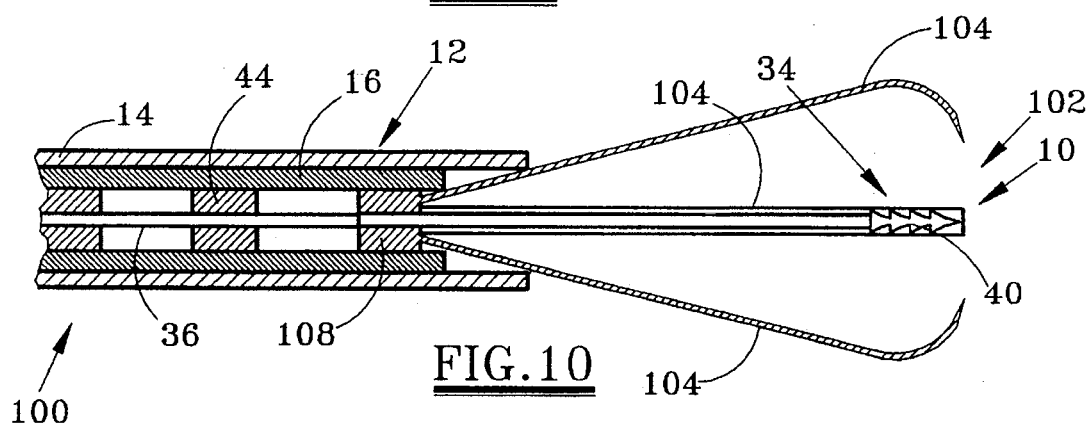
FIG. 10 is a side cross-sectional view of the distal end of the forceps embodiment of FIG. 9 with the jaws open.
Figure 11:
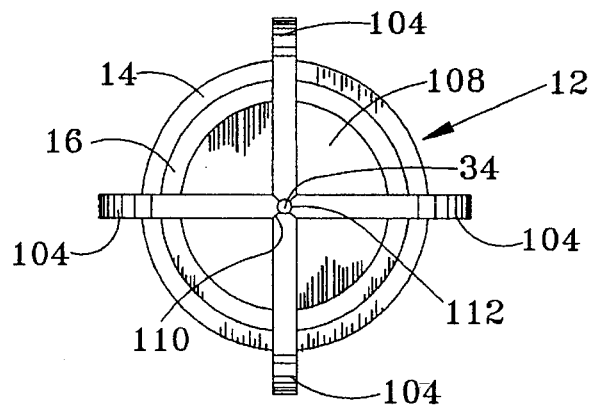
FIG. 11 is a front view of the forceps of FIG. 9.
Figure 12:
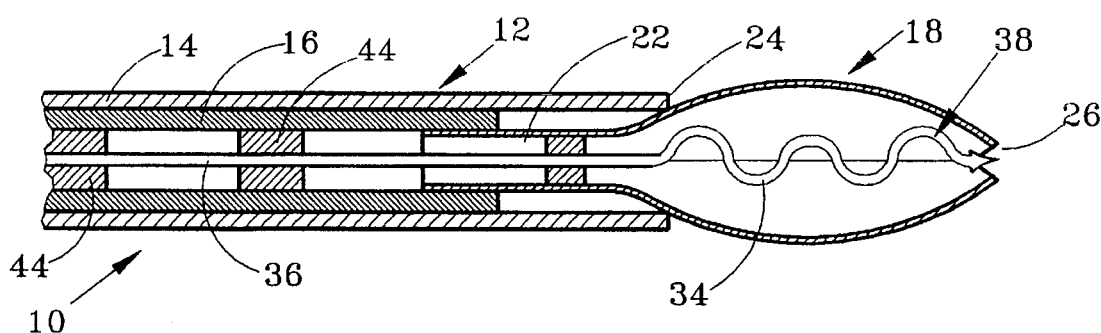
FIG. 12 is a side cross-sectional view of an alternate embodiment of the distal end of the multiple biopsy forceps of FIG. 1 equipped with a needle having a helical section and a terminal barb which function as a retaining element.

Referring to FIGS. 9–11, an embodiment 100 of the present biopsy forceps having a talon shaped jaws 102 can be seen. The talon type jaws 102 comprises two of more pairs of cooperating prongs 104 which intersect at a mouth 106 to grasp the biopsy specimen. The prongs 104 are preferably attached to a neck 108 under spring tension so that the jaws 102 have an open bias with no force exterted thereon. The jaws 102 are preferably mounted to the inner tube 16 by fixedly inserting the neck 108 into the annular region of the inner tube 16. Thus, longitudinally sliding the inner and outer tubes 14, 16 relative to each other draws the neck 108 into the annular region of the outer tube 14 and causes an end wall 24 thereof to exert sufficient force on the spring biased prongs 104 to effect closure of the jaws 102. The jaws 102 are typically made of a metallic material such as stainless steel to impart a spring bias to the prongs 104.

The mouth 106 is suitable for grasping the tissue sample for biopsy from the organ wall when the jaws 102 are closed. The mouth 106 includes pairs of pincer members 110 located around an opening 112 through which the needle 34 can pass to transfix and retain the acquired tissue sample.

The multiple biopsy forceps 10 of the present invention can be made to be disposable. The tubular body 12 can be made of a rigid but flexible plastic such as polypropylene, polyethylene, polyacrylic, and the like or a metallic material, so that the diameter of the body 12 is rigid for good slideability but flexible along the length for ease of passage through the endoscope, especially when acutely angled.

Figure 5:
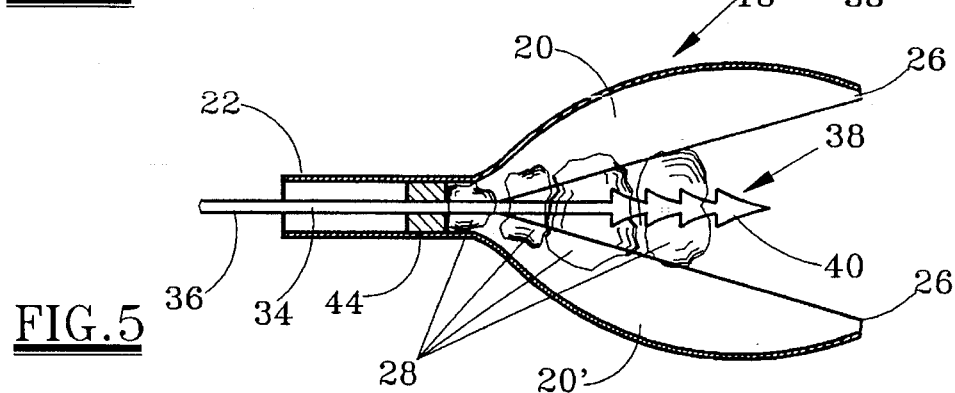
FIG. 5 is a side cross-sectional view of the jaws of FIGS. 3–4 with the jaws opened after a series of tissue samples have been removed and transfixed by the needle.
Figure 6:
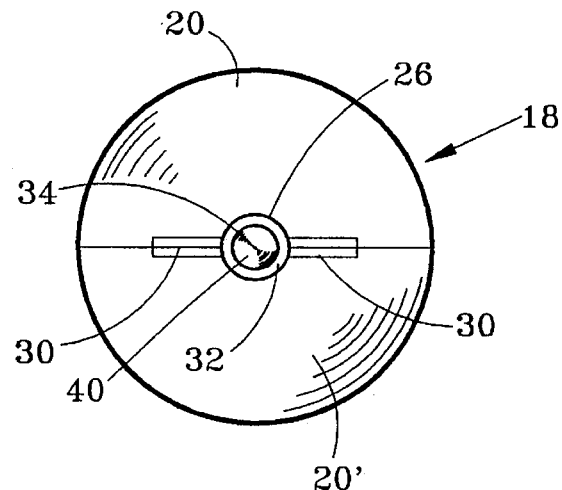
FIG. 6 is a front view of the jaws of FIGS. 3–5 showing the jaw opening for the needle.
Figure 7:
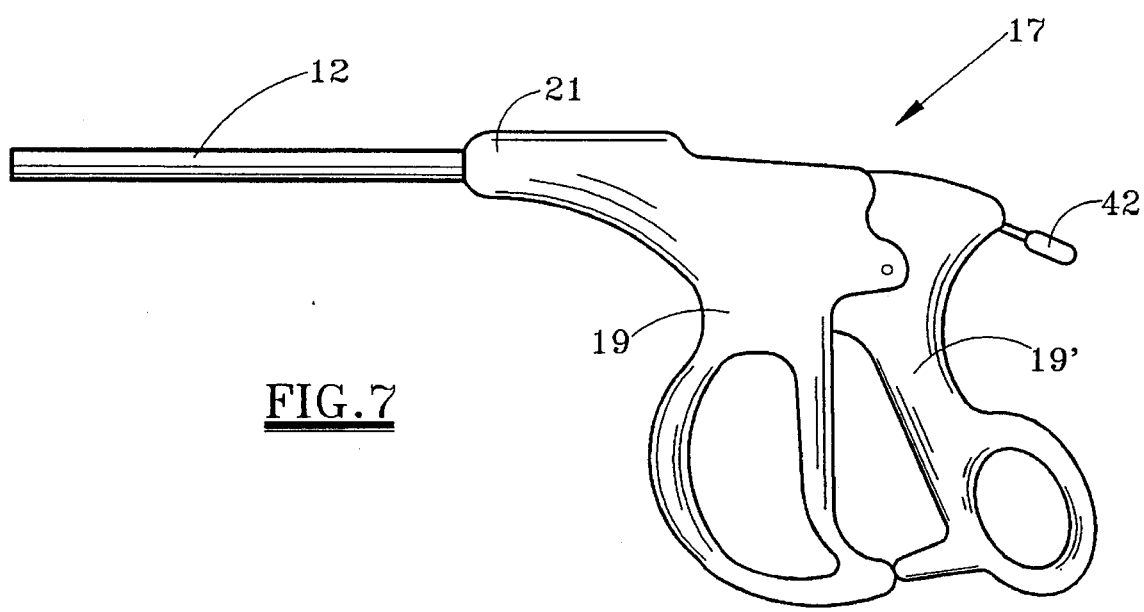
FIG. 7 is a schematic side view of a proximal end of the multiple biopsy forceps of FIG. 1 showing the activating handle for the outer and inner tubes, jaws and needle.
Figure 8:
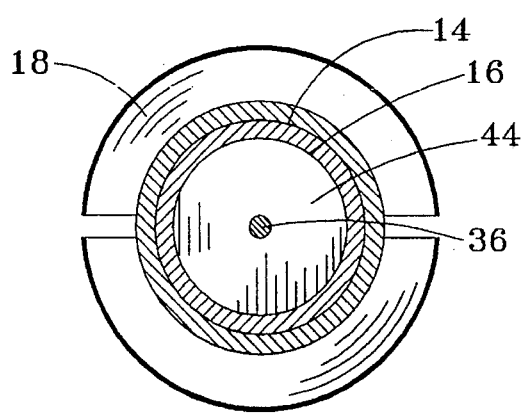
FIG. 8 is a radial cross-sectional view of the multiple biopsy forceps of the present invention along the lines 8—8 in FIG. 2.

The present forceps 10, 100 which are useful for obtaining multiple samples in a single passage through the endoscope has suitable means to identify each particular sample 28 of the series thereof on the needle 34 (as seen in FIG. 5) to the organ tissue from which it is taken. To this end, the outer and inner tubes 14, 16 typically have distance graduation marks (such as centimeters, not shown) formed thereon so that each sample 28 can be identified by a distance along the endoscope.

To use the biopsy forceps of the present invention to take multiple specimens for biopsy per passage through the endoscope, the clinician having inserted the endoscope into the patient and observed diseased tissue for biopsy then inserts the present forceps 10, 100 through the endoscope biopsy channel. The endoscope is used to guide the jaws 18, 102 of the forceps 10, 100 to the organ tissue to be biopsied. An adjustment of the position of the jaws can be made either by manipulating the length of the endoscope in the patient or the forceps body 12 in the endoscope channel.

Once the jaws 18, 102 are positioned in abutment to the tissue to be biopsied, the handle 17 is operated to close the jaws 18, 102 around a sample of the tissue. Generally the pincers 30, 110 grasp the tissue 28 from either side when the jaws 18, 102 are closed. The needle handle 42 is manipulated to advance the needle 34 through the jaws opening 32, 112 and transfix the grasped sample 28 in the jaws 18, 102. A slight tug on the body 12 of the forceps 10 tears the sample 28 from the organ wall 29. The length of the forceps 10 and endoscope are noted by reading the graduation marks thereon to identify the sample 28 for biopsy and the tissue from whence the sample was taken. It can be seen that extant samples 28 previously collected are forced rearward on the needle barbs 40 when the needle 34 is advanced through the jaws opening 32, 112. The jaws 18, 102 are then opened, the needle 34 is retracted by manipulation of the handles 17, 42 and the forceps 10 is repositioned using the endoscope to view a new tissue area to be biopsied. Another sample can be taken by repeating the steps detailed above.

After no additional biopsy samples are required, the forceps is removed from the endoscope biopsy channel and the tissue samples 28 are removed from the needle 34 and catalogued to the area 29 of the organ tissue sampled. Between patients, a disposable forceps which is used should be properly disposed of and non-disposable forceps should be sterilized.

The foregoing description of the invention is illustrative and explanatory thereof. Various changes in the materials, apparatus, and particular parts employed will occur to those skilled in the art. It is intended that all such variations within the scope and spirit of the appended claims be embraced thereby.

I claim:

1. A biopsy forceps for obtaining multiple tissue specimens of an organ through a biopsy channel of an endoscope, comprising:

a tubular body having a length and outside diameter for passage through the biopsy channel;

a set of jaws mounted on a distal end of the body;

means for operating the jaws to grasp and remove a tissue specimen;

a needle centrally received through the body and slideable therethrough, wherein the needle is operable independently of the jaws to transfix a tissue specimen while the specimen is held by the set of jaws;

a retaining element adjacent a distal end of the needle to sequentially collect a plurality of tissue specimens on the needle; and a proximal activating handle for independently operating the jaws and needle.

2. The forceps of claim 1, wherein the jaws are closed by activation of a cable actuator disposed in the tube body.

3. A biopsy forceps for obtaining multiple tissue specimens of an organ through a biopsy channel of an endoscope, comprising:

an outer tube having a length and outside diameter for passage through the biopsy channel;

an inner tube concentric with the outer tube and slideably received therein;

a set of jaws mounted on a distal end of the inner tube operable by longitudinally sliding the inner and outer tubes with respect to each other to grasp and remove a tissue specimen;

a needle centrally received through the body and slideable therethrough, wherein the needle is operable independently of the jaws to transfix a tissue specimen while the specimen is held by the set of jaws;

a retaining element adjacent a distal end of the needle to sequentially collect a plurality of tissue specimens on the needle; and proximal activating handles for operating the inner and outer tubes, jaws and needle.

4. The forceps of claim 3 made of a disposable material.

5. The forceps of claim 4, wherein the inner and outer tubes are made of a substantially rigid plastic material which is flexible along the biopsy channel of the endoscope.

6. The forceps of claim 3, including graduation markings on the tubes for identifying the tissue location of each specimen collected.

7. The forceps of claim 3, wherein the jaws are cusp shaped, include a cutting edge and are made from a metallic or ceramic material.

8. The forceps of claim 7, wherein the jaws are talon shaped.

9. The forceps of claim 3, wherein the retaining element includes a barb.

10. The forceps of claim 3, wherein the retaining element includes a helical configuration of the needle.

11. The forceps of claim 3, wherein the needle is attached to a distal end of a wire slideably disposed in the inner tube.

12. The forceps of claim 11, wherein the proximal handle manually advances and retracts the wire in sequence with the closing and opening of the jaws.

13. A method for obtaining multiple tissue biopsies of an organ through an endoscope, comprising the sequential steps of:

(a) inserting an endoscope having a biopsy channel to visualize an area to be biopsied;

(b) inserting the biopsy forceps of claim 1 through the biopsy channel;

(c) placing the jaws in contact with tissue to be biopsied;

(d) operating the jaws to grasp a sample of the tissue to be biopsied;

(e) transfixing the grasped tissue with the needle to engage the tissue sample with the retaining element;

(f) repeating steps (c) through (e) to sequentially collect a plurality of tissue samples on the needle; and (g) withdrawing the biopsy forceps from the biopsy channel to retrieve the tissue samples.

14. A method for obtaining multiple tissue biopsies of an organ through an endoscope, comprising the sequential steps of:

(a) inserting an endoscope having a biopsy channel to visualize an area to be biopsied;

(b) inserting an outer tube through the biopsy channel, the outer tube including an inner tube concentric therewith and slideably received therein;

(c) placing jaws mounted on a distal end of the inner tube in contact with tissue to be biopsied, the jaws operable by longitudinally sliding the inner and outer tubes with respect to each other;

(d) operating the jaws to grasp a sample of the tissue to be biopsied;

(e) transfixing the grasped tissue with a needle to engage the tissue sample with a retaining element thereon, the needle centrally received through the inner tube and slideable therethrough, wherein the needle is operable independently of the jaws;

(f) repeating steps (c) through (e) to sequentially collect a plurality of tissue samples on the needle; and (g) withdrawing the biopsy forceps from the biopsy channel to retrieve the tissue samples.

15. The method of claim 14, including reading graduation markings on the tubes for identifying the tissue location of each sample collected after the transfixing step (e).

16. The method of claim 15, wherein the jaws are attached to the inner tube and the operating step (d) includes the step of slideably retracting the inner tube with respect to the outer tube or slideably advancing the outer tube with respect to the inner tube to close the jaws.

17. The method of claim 16, wherein the retaining element includes a plurality of barbs.

18. The method of claim 16, wherein the retaining element includes a helical configuration of the needle.

19. The method of claim 16, wherein the needle is attached at a distal end of a wire slideably mounted in the inner tube.

20. The method of claim 19, wherein the transfixing step (d) includes the step of manually advancing and retracting the wire in sequence with the jaw operating step.

21. The method of claim 20, wherein the operating and transfixing steps (d–e) are effected by manipulating a proximal activating handle.

* * * * *